United States Patent
Imbert et al.

[11] Patent Number: 5,958,945
[45] Date of Patent: Sep. 28, 1999

[54] NAPHTHAMIDE DERIVATIVES OF 3-BETA-AMINO AZABICYCLO OCTANE OR NONANE AS NEUROLEPTIC AGENTS

[75] Inventors: Thierry Imbert, Viviers-les-Montagnes; Barbara Monse, Castres; Wouter Koek, Viviers-les-Montagnes, all of France

[73] Assignee: Pierre Fabre Medicament, Boulogne, France

[21] Appl. No.: 09/029,693

[22] PCT Filed: Sep. 11, 1996

[86] PCT No.: PCT/FR96/01394

§ 371 Date: Mar. 12, 1998

§ 102(e) Date: Mar. 12, 1998

[87] PCT Pub. No.: WO97/10244

PCT Pub. Date: Mar. 20, 1997

[30] Foreign Application Priority Data

Sep. 12, 1995 [FR] France ................................. 95 10655

[51] Int. Cl.[6] ................ C07D 451/04; C07D 451/14; A61K 31/435; A61K 31/44
[52] U.S. Cl. ............... 514/304; 514/299; 546/112; 546/132
[58] Field of Search .................... 546/132, 112; 514/304, 299

[56] References Cited

U.S. PATENT DOCUMENTS 5,395,835  3/1995  Glase ........................... 514/254

FOREIGN PATENT DOCUMENTS 0076592  4/1983  European Pat. Off. .
0539281  4/1993  European Pat. Off. .
0585116  3/1994  European Pat. Off. .

*Primary Examiner*—Alan L. Rotman
*Attorney, Agent, or Firm*—The Firm of Gordon W. Hueschen

[57] ABSTRACT

The invention pertains to novel azabicyclo-naphthalene-carboxamide derivatives, a method for preparing same and the use thereof as a medicament. The compounds of the invention are of formula (I).

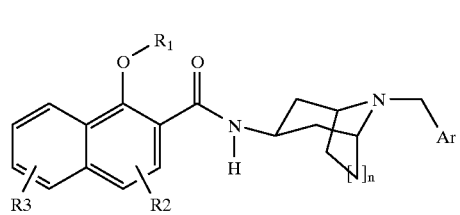

10 Claims, No Drawings

NAPHTHAMIDE DERIVATIVES OF 3-BETA-AMINO AZABICYCLO OCTANE OR NONANE AS NEUROLEPTIC AGENTS

CROSS REFERENCE

The present application is a U.S. National Application filed under 35 USC 371 of PCT/FR96/01394, filed Sep. 11, 1996.

The present invention relates to novel azabicyclonaphthalenecarboxamide derivatives, to a process for their preparation and to their use as drugs.

These compounds are antidopaminergic and antiserotoninergic agents and are thus used as antipsychotic drugs for treating schizophrenia, its positive and negative symptoms, or disorders of the central nervous system that are sensitive to antidopaminergic and antiserotoninergic treatment, such as, for example, compulsive obsessive disorders, anxiety, depression, drug addiction, tardive dyskinesia and gastrointestinal disorders.

The need to have antidopaminergic activity, in particular on the dopaminergic receptors of the subclass $D_2$, constitutes a standard approach in the treatment of schizophrenia (Carlsson A., Am. J. Psychiatry, 135, 164, 1978). However, most of the compounds having such a mechanism of action have the drawback of possessing undesirable clinical side effects, in particular extrapyramidal side effects (see Acta Psychiatr. Scand. 1995, 91 (Suppl 388): 24–30).

It has been seen that the fact of combining with powerful antidopaminergic activity, in the same molecule, antagonist activity towards the serotoninergic receptors of the $5-HT_2$ subclass might constitute a condition for avoiding these extrapyramidal side effects (H. Y. Meltzer J.P.E.T. 1989, 251, 238).

U.S. Pat. No. 5,395,835 describes naphthamides of formula

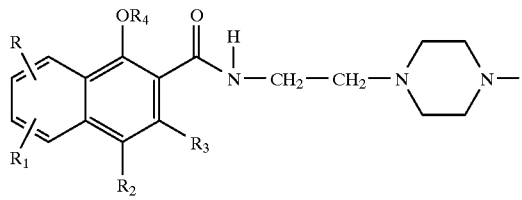

in which the naphthalene ring-system is variously substituted with variable groups R, these products being antidopaminergic agents of the $D_3$ subclass, which are useful as antipsychotic agents for the treatment of schizophrenia or other pathologies which respond to blocking of the dopaminergic receptors.

Patent EP 539,281 describes naphthamides of formula

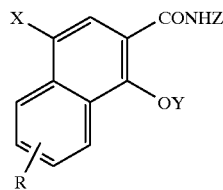

in which Z represents a residue derived from 2-aminomethyl-N-alkylpyrrolidine, 2-aminoethyl-N,N-diethylamine, 2-aminoethylmorpholine, 2-aminoethyl-N,N-dibutylamine or 4-amino-N-butyl (or N-benzyl) piperidine, which are active on the dopaminergic system, in particular the $D_3$ receptor subclass, and are useful as antipsychotic agents, psychostimulants, antiautistic agents, antidepressants, anti-Parkinson agents and antihypertensive agents. The compound which is structurally most similar to the compounds of the present invention corresponds to the above structure in which R=H, Y=CH_3, X=H, and Z=4-amino-N-benzylpiperidine, and will be referred to hereinbelow as: patent EP 539,281 compound.

Patent EP 585,116 describes 1-alkoxynaphthalene-2-carboxamides, with a high degree of affinity for the $5-HT_{1A}$ serotoninergic receptors, of formula

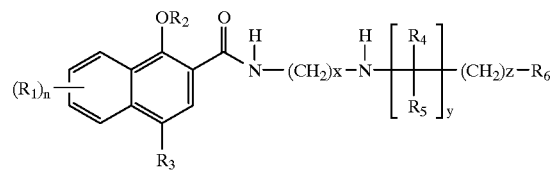

U.S. Pat. No. 4,536,580 describes nortropane benzamide derivatives with neuroleptic properties, of formula

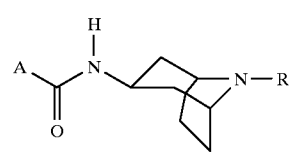

where A represents a variously substituted pyrimidine or benzene ring, the most powerful product being compound No. 64 (tropapride) (Drug of the Future, Vol. 9, No. 9, 673).

Patent EP 416,521 describes compounds of naphthamide tropane type, of structure:

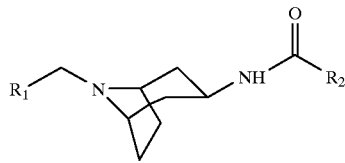

where $R_2$ may be a naphthalene ring-system, which is either unsubstituted or substituted with an alkyl group of 1 to 10 carbon atoms. These compounds are active in the cardiovascular field.

Patent WO 84/03281 describes compounds of azabicycloalkylbenzamide type, of formula

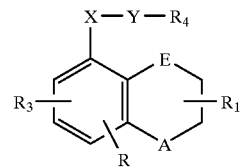

where $R_4$ may be a tropane skeleton and the ring formed by the junction A—E may be a heterocycle and form a quinoline.

However, it does not appear, or is not suggested in the abovementioned patents, that the fact of combining a 3-β-aminotropane skeleton with an aromatic 1-alkoxy-2-naphthamide system can give compounds having this double activity: simultaneously dopaminergic antagonist and agonist on the $D_2$ subclass, and simultaneously serotoninergic antagonist and agonist, this being the basis of the present invention.

The best balance represented by the derivatives of the invention between the serotoninergic receptors, in particular, but not exclusively, the 5-$HT_2$ receptors, in comparison with the dopaminergic $D_2$ receptors, makes it possible to highlight the clinical advantage of these products in man, combining the therapeutic efficacy associated with a low propensity to manifest extrapyramidal side effects (Meltzer H. Y. Psychopharmacology, 1989, 99, 18–27 and Meltzer H. Y. J. Clin. Psychopharmacology, 15 suppl. 1: 1S, 1995).

The best compound currently used and corresponding to the criteria thus defined is Risperidone, of structure:

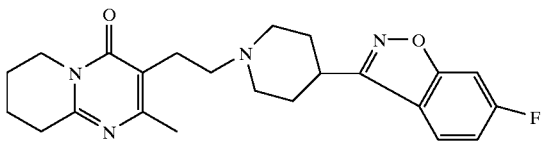

The subject of the present invention is novel substituted 3-β-aminotropane-8-benzyl derivatives of substituted 1-alkoxy-2-naphthamide, to a process for their preparation, to their pharmaceutically acceptable salt form, to pharmaceutical compositions containing them and to their application as antipsychotic drugs in human therapy.

These novel compounds correspond to the general formula I

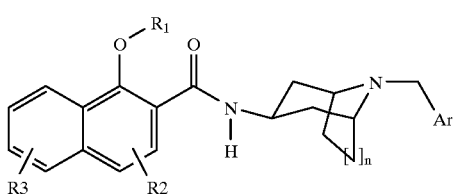

in which Ar represents an aromatic residue such as, for example, a phenyl or heteroaryl ring, the phenyl ring being unsubstituted or substituted with one or more substituents chosen from $C_{1-4}$ alkyl, Cl, F or Br halogen or $C_{1-4}$ O-alkyl, it being possible for n to be one or two and thus to form an 8-azabicyclo[3.2.1]octane or a 9-azabicyclo-[3.3.1]nonane, $R_1$ represents a linear or branched $C^{1-6}$ alkyl group, it being possible for $R_2$ and $R_3$, which may be identical or different, borne by the carbons of the aromatic ring, each to be H, Cl, Br, F, $C_{1-4}$ alkyl, OH, CN, $NO_2$, $C_{1-4}$ alkylthio, $NH_2$, $C_{1-4}$ alkylamino, $C_{1-4}$ dialkylamino, acylamino, $SO_2NH_2$, $C_{1-4}$ $SO_2$N-dialkyl or $C_{1-4}$ $SO_2$-alkyl.

Preferably, the group Ar is a phenyl which is unsubstituted or substituted with a halogen, the substituent $R_1$ can be a methyl or an ethyl, the substituent $R_2$ in position 4 preferably being an H, Br, Cl, F, $NO_2$, $NH_2$, $NMe_2$, CN, $OCH_3$ or OH, and thus correspond to the following compounds:

1-methoxy-4-(N,N-dimethylaminosulfonyl)-N-[8-(phenylmethyl)-8-azabicyclo[3.2.1]oct-3-b-yl]-2-naphthalenecarboxamide
1,3-dimethoxy-N-[8-(phenylmethyl)-8-azabicyclo[3.2.1]oct-3-b-yl]-2-naphthalenecarboxamide
1-methoxy-N-[8-(phenylmethyl)-8-azabicyclo[3.2.1]oct-3-b-yl]-2-naphthalene-carboxamide.
4-bromo-1-methoxy-N-[8-(phenylmethyl)-8-azabicyclo[3.2.1]oct-3-b-yl]-2-naphthalenecarboxamide
4-chloro-1-methoxy-N-[8-(phenylmethyl)-8-azabicyclo[3.2.1]oct-3-b-yl]-2-naphthalenecarboxamide
1-methoxy-4-(N,N-dimethylamino)-N-[8-(phenylmethyl)-8-azabicyclo[3.2.1]oct-3-b-yl]-2-naphthalenecarboxamide
4-amino-1-methoxy-N-[8-(phenylmethyl)-8-azabicyclo[3.2.1]oct-3-b-yl]-2-naphthalenecarboxamide
1-methoxy-4-nitro-N-[8-(phenylmethyl)-8-azabicyclo[3.2.1]oct-3-b-yl]-2-naphthalenecarboxamide
4-cyano-1-methoxy-N-[8-(phenylmethyl)-8-azabicyclo[3.2.1]oct-3-b-yl]-2-naphthalenecarboxamide
1,5-dimethoxy-N-[8-(phenylmethyl)-8-azabicyclo[3.2.1]oct-3-b-yl]-2-naphthalenecarboxamide
1,4-dimethoxy-N-[8-(phenylmethyl)-8-azabicyclo[3.2.1]oct-3-b-yl]-2-naphthalenecarboxamide
1-ethoxy-N-[8-(phenylmethyl)-8-azabicyclo[3.2.1]oct-3-b-yl]-2-naphthalenecarboxamide
4-bromo-1-ethoxy-N-[8-(phenylmethyl)-8-azabicyclo[3.2.1]oct-3-b-yl]-2-naphthalenecarboxamide
4-acetamido-1-methoxy-N-[8-(phenylmethyl)-8-azabicyclo[3.2.1]oct-3-b-yl]-2-naphthalenecarboxamide
4-acetamido-1-methoxy-N-[8-(4-fluorophenylmethyl)-8-azabicyclo[3.2.1]oct-3-b-yl]-2-naphthalenecarboxamide
4-acetamido-1-methoxy-N-[8-(4-chlorophenylmethyl)-8-azabicyclo[3.2.1]oct-3-b-yl-]2-naphthalenecarboxamide
4-amino-1-methoxy-N-[8-(4-chlorophenylmethyl)-8-azabicyclo[3.2.1]oct-3-b-yl]-2-naphthalenecarboxamide
4-amino-1-methoxy-N-[8-(4-fluorophenylmethyl)-8-azabicyclo[3.2.1]oct-3-b-yl]-2-naphthalenecarboxamide
4-amino-1-ethoxy-N-[8-(4-fluorophenylmethyl)-8-azabicyclo[3.2.1]oct-3-b-yl]-2-naphthalenecarboxamide
4-fluoro-1-ethoxy-N-[8-(phenylmethyl)-8-azabicyclo[3.2.1]oct-3-b-yl]-2-naphthalenecarboxamide
4-fluoro-1-methoxy-N-[8-(phenylmethyl)-8-azabicyclo[3.2.1]oct-3-b-yl]-2-naphthalenecarboxamide
4-bromo-1-methoxy-N-[9-(phenylmethyl)-9-azabicyclo[3.3.1]non-3-b-yl]-2-naphthalenecarboxamide
4-amino-1-methoxy-N-[9-(phenylmethyl)-9-azabicyclo[3.3.1]non-3-b-yl]-2-naphthalenecarboxamide
4-bromo-1-methoxy-N-[8-(4-fluorophenylmethyl)-8-azabicyclo[3.2.1]oct-3-b-yl]-2-naphthalenecarboxamide
4-bromo-1-methoxy-N-[8-(4-chlorophenylmethyl)-8-azabicyclo[3.2.1]oct-3-b-yl]-2-naphthalenecarboxamide
4-methylthio-1-methoxy-N-[8-(phenylmethyl)-8-azabicyclo[3.2.1]oct-3-b-yl]-2-naphthalenecarboxamide
4-ethylthio-1-methoxy-N-[8-(phenylmethyl)-8-azabicyclo[3.2.1]oct-3-b-yl]-2-naphthalenecarboxamide
4-ethylsulfonyl-1-methoxy-N-[8-(phenylmethyl)-8-azabicyclo[3.2.1]oct-3-b-yl]-2-naphthalenecarboxamide
4-aminosulfonyl-1-methoxy-N-[8-(phenylmethyl)-8-azabicyclo[3.2.1]oct-3-b-yl]-2-naphthalenecarboxamide
4-hydroxy-1-methoxy-N-[8-(phenylmethyl)-8-azabicyclo[3.2.1]oct-3-b-yl]-2-naphthalenecarboxamide
4-hydroxy-1-ethoxy-N-[8-(phenylmethyl)-8-azabicyclo[3.2.1]oct-3-b-yl]-2-naphthalenecarboxamide
1-methoxy-N-[9-(phenylmethyl)-9-azabicyclo[3.3.1]-non-3β-yl]-2-naphthalenecarboxamide
1-ethoxy-4-nitro-N-[8-(phenylmethyl)-8-azabicyclo[3.2.1]oct-3β-yl]-2-naphthalenecarboxamide The compounds of the present invention can form salts by addition of pharmaceutically acceptable inorganic or organic acid and can be incorporated in pharmaceutical compositions so that they can be administered via the various usual routes, in oral, injectable or parenteral form.

The demonstration of the antidopaminergic and antiserotinergic properties of the compounds of the invention is made on the basis of their affinity for the corresponding receptors by displacement of the radioactive ligand which specifically label these receptors ([$^3$H] YM-09151-2 for the $D_2$ receptor and [$^3$H] Ketanserine for the 5-HT$_2$ receptor).

This process for studying specific binding is described Naunyn-Schmiedeberg's Arch. Pharmacol. 329, 333–338, 1985 and Mol. Pharmacol. 21, 301–314, 1982.

By way of example, the values are indicated in the following table by comparison with reference substances:

| Compound | Binding to the $K_i$ receptor (M) | |
| --- | --- | --- |
| | $D_2$ site Ligand [$^3$H] YM09151-2 Ki | 5-HT$_2$ site Ligand [$^3$H] Ketanserine Ki |
| Sulpiride | 4.63 × 10$^{-9}$M | >10$^{-5}$M |
| Risperidone | 2.00 × 10$^{-9}$M | 2.74 × 10$^{-9}$M |
| Tropapride U.S. Pat. No. 4,536,580 | 1.06 × 10$^{-10}$M | 2.94 × 10$^{-7}$M |
| Patent EP 539,281 compound | 3.32 × 10$^{-9}$M | 1.29 × 10$^{-6}$M |
| Example 3 | 1.43 × 10$^{-10}$M | 6.68 × 10$^{-8}$M |
| Example 5 | 4.08 × 10$^{-10}$M | 1.64 × 10$^{-8}$M |
| Example 4 | 7.76 × 10$^{-10}$M | 3.76 × 10$^{-9}$M |
| Example 13 | 9.44 × 10$^{-10}$M | 7.79 × 10$^{-9}$M |

It emerges from this study, surprisingly, that the compounds of the invention with a structure according to formula I have affinities for the two receptors $D_2$ and 5-HT$_2$, as can be seen from the table, when compared with the reference substances: Sulpiride, the antipsychotic compound usually used, Risperidone, an atypical antipsychotic compound as defined by H. Y. Meltzer, Tropapride (U.S. Pat. No. 4,536,580), and the patent EP 539,281 compound, which have little or no 5-HT$_2$ affinity.

The advantage of the compounds of the invention is seen in the greater affinity, 10 to 100 times greater, which they manifest for the 5-HT$_2$ serotoninergic receptors when compared with Tropapride or with the patent EP 539,281 compound, and they have a better balance between the dopaminergic and serotoninergic receptors, which makes it possible to obtain compounds having a better clinical profile, in order not only to have the power of the antipsychotic effects but also the absence of the undesirable side effects.

The in vivo test, performed on rats, showing the antipsychotic activity is that of inhibition of the behavior induced by methylphenidate according to the method described by W. Koek and F. C. Colpaert in J. Pharmacol. Exp. Ther. 1993, 267, 181.

The results obtained showed that the compounds of the invention are capable not only of inhibiting the stereotypical machonnement but also of normalizing all the behavior induced by methylphenidate, and of achieving this in the absence of undesirable side effects.

This test characterizes the antipsychotic activity of the compounds in greater depth than the antagonism of the effects of apomorphine, which is the test conventionally used.

The present invention thus relates to compounds of general formula I as drugs that are useful in particular in the treatment of schizophrenia.

The present invention also relates to the use of compounds of general formula I incorporated in a pharmaceutical composition with a formulation corresponding to its mode of administration: tablets, wafer capsules or gelatin capsules, suitable for human clinical treatment and at daily doses of between 0.1 and 500 mg or more specifically 0.1 to 100 mg of active principle.

The products of the present invention are obtained by known processes, the key step of which is the formation of the amide function between the 1-alkoxy-2-naphthoic acid of formula II and the amine of formula III

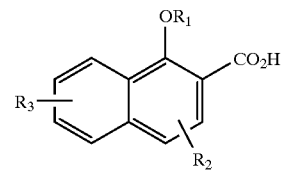

The values of $R_1$, $R_2$ and $R_3$ are the same as those of general formula I. These acids are either known in the chemical literature or are prepared by the usual methods, by analogy with substituted benzoic acids (of the salicylic type).

For example, the benzoic acid II where $R_1=CH_3$; $R_2=R_3=H$, is described in Monatshef. Chem. 1884, 15, 735 where $R_1=CH_3$; $R_2=4-NO_2$; $R_3=H$, is described in Indian Acad. Sci. Sect. A 1938, 7, 261 where $R_1=CH_3$; $R_2=H$; $R_3=5-OCH_3$, is described in J. Chem. Soc 1937, 937–940 where $R_1=C_2H_5$; $R_2=R_3=H$, is described in Austr. J. Chem. 1974, 27, 2209 where $R_1=CH_3$; $R_2=4-Br$; $R_3=H$, is described in J. Indian Chem. Soc. 1936, 13, 645.

Similarly, the acid II in which $R_1=C_2H_5$; $R_2=4-Br$; $R_3=H$ is prepared, in the same article the acid II in which $R_1=CH_3$; $R_2=4-Cl$; $R_3=H$ is prepared, the acid II in which $R_1=CH_3$; $R_2=4-OH$; $R_3=H$, is described in J. Am. Chem. Soc. 1942, 64, 798–800 and in which $R_1=CH_3$; $R_2=4-NH_2$; $R_3=H$, is described in J. Chem. Soc. 1922, 1658, similarly, in which $R_1=CH_3$; $R_2=4-OCH_3$; $R_3=H$, is described in J. Organomet. Chem. 1969, 20, 251; in which $R_1=CH_3$; $R_2=3-OCH_3$; $R_3=H$, is described in J. Am. Chem. Soc. 1952, 74, 1624, in which $R_1=CH_3$; $R_2=4-NMe_2$; $R_3=H$, is described in patent EP 585,116. The acid II in which $R_1=CH_3$; $R_2=4-CN$; $R_3=H$ is obtained by the standard Sandmeyer reaction starting with the 4-amino derivative described in patent EP 539,281.

The acid II in which $R_1=CH_3$; $R_2=SCH_3$; $SC_2H_5$, $SO_2CH_3$, $SO_2C_2H_5$ or $SO_2-NH_2$ is obtained according to the process described in the patents Be 874,490 or Spain 454,931 on the 2-alkoxybenzoic acids, by reaction with sulfuric chlorohydrin, and in order to obtain the 4-SO$_2$Cl derivative which is reduced by dimerizing into a dithio derivative, from which the methylthio or ethylthio derivative can be obtained by treatment with alkyl halide in basic medium. By oxidation using potassium permanganate or using peracids such as metachloroperbenzoic acid, the corresponding sulfonyl substituents can be obtained.

The 3β-amino-8-azabicyclo[3.2.1]octane-8-benzyl polycyclic amine of formula III (n=1) is prepared according to the described process (Eur. J. Med. Chim. 1984, 19, 105).

The 3β-amino-9-azabicyclo[3.3.1]nonane-9-benzyl polycyclic amine of formula III (n=2) is prepared by direct analogy and according to the process described in J. Org. Chem. 26, 395, 1961.

III

[Structure: H₂N-substituted bicyclic amine with N-CH₂-Ar group]

Ar has the same characteristic as that mentioned for formula I.

The condensation of the acid II and the amine III is carried out by activating the acid II either via its acid chloride, for example the acid chloride of the corresponding naphthenic acid, or via the mixed anhydride obtained by reaction of the acid II with an alkyl, for example ethyl, chloroformate at 0° C. in the presence of a base such as triethylamine in methylene chloride or another inert solvent, followed by a reaction with the amine of formula III.

The $NH_2$ derivative in position 4 can be acetylated under the usual conditions, i.e. with acetic anhydride alone or in pyridine, or alternatively with acetyl chloride in $CH_2Cl_2$ or THF in the presence of a base such as triethylamine or $K_2CO_3$.

The debenzylation of the N-benzyl function of the heterocycle can be carried out in the presence of hydrogen over 10% palladium-on-charcoal in neutral or acidic medium, optionally under pressure in an autoclave. In the case of the compounds halogenated in position 4, the method of dealkylation with α-chloroethyl chloroformate is used as indicated in J. Org. Chem. 1984, 49, 2081.

The alkylation of the resulting secondary amine with a substituted benzyl chloride is carried out conventionally in refluxing acetonitrile optionally in the presence of a base such as $K_2CO_3$. The deacetylation of the aniline in position 4 can take place by heating in acidic medium, for example aqueous hydrochloric acid, in a water-miscible solvent such as ethanol.

The fluorination in position 4 can also be carried out conventionally as indicated in Organic Syntheses Coll. Vol. II, p. 299, by decomposition of the diazonium tetrafluoroborate on the corresponding naphthenic ester.

The phenolic derivatives in position 4 of the naphthalene ring-system are obtained by hydrogenolysis of the derivatives protected with a benzyl or benzyl carbonate group, by hydrogen in the presence of 10% palladium-on-charcoal (T.N. Greene Protective Groups in Organic Synthesis 1991, p. 156 and 157) starting with the compounds I in which $R_1=CH_3$; $R_2=OCH_2Ph$; $R_3=H$; in the present case, the N-benzyl function is not affected by these hydrogenolysis conditions.

The known acid II in which $R_1=CH_3$; $R_2=4$-OH; $R_3=H$ is protected with one of the abovementioned protecting groups before the amidation step.

The examples which follow are given as non-limiting examples:

EXAMPLE 1

1-Methoxy-4-(N,N-dimethylaminosulfonyl)-N-[8-(phenylmethyl)-8-azabicyclo[3.2.1]oct-3-β-yl]-2-naphthalenecarboxamide hydrochloride. (Formula I: $R_1=CH_3$; $R_2=4$-$SO_2N(CH_3)_2$; $R_3=H$; Ar=Ph; n=1)

Stage 1: Methyl 1-methoxy-4-(N,N-dimethylaminosulfonyl)-2-naphthalenecarboxylate.

A mixture of 2.0 g of 4-aminosulfonyl-1-hydroxy-2-naphthoic acid (7.48 mmol; 1 eq) with 3.0 ml of dimethyl sulfate (32 mmol; 4.2 eq) and 4.65 g of potassium carbonate (33.7 mmol; 4.5 eq) is refluxed in 100 ml of acetone overnight. The precipitate is filtered off and the solvent is evaporated off under vacuum. The residue is taken up in ethyl acetate, washed several times with water and dried over $Na_2SO_4$ and the solvent is evaporated off under vacuum.

2.3 g of the pure product (95%) are obtained. NMR (1H; $CDCl_3$); 2.79 (s; 6H; N—$(CH_3)_2$), 3.97 (s; 3H; $C(O)OCH_3$), 4.10 (s; 3H; $OCH_3$); 7.59–7.77 (m; 2H), 8.37 (dd, J=7.7, 1.6 Hz; 1H), 8.56 (s; 1H) 8.70 (dd, J=7.7, 1.6 Hz; 1H).

Stage 2: 1-Methoxy-4-(N,N-dimethylaminosulfonyl)-2-naphthalenecarboxylic acid

A solution of methyl 1-methoxy-4-(N,N-dimethylaminosulfonyl)-2-napthalenecarboxylate (2.3 g; 7.13 mmol; 1 eq) is refluxed in 50% ethanol with 428 mg of NaOH (10.71 mmol; 1.5 eq) for 2 h. Next, the solvent is evaporated off under vacuum and the residue is taken up in water and extracted once with ethyl acetate. 1N HCl is added to the aqueous phase to pH 1–2. The mixture is extracted twice with dichloromethane, dried and evaporated.

1.92 g of the pure acid (87%) are obtained. NMR (1H; DMSO-$d_6$): 2.75 (s; 6H; $N(CH_3)_2$), 4.08 (s; 3H; $OCH_3$), 7.74–7.92 (m; 2H), 8.39 (d, J=7.9 Hz; 1H), 8.40 (s; 1H), 8.65 (d, J=7.9 Hz; 1H), 13.57 (s; 1H; COOH).

Stage 3: 1-Methoxy-4-(N,N-dimethylaminosulfonyl)-N-[8-phenylmethyl)-8-azabicyclo[3.2.1]oct-3-β-yl]-2-naphthalenecarboxamide hydrochloride 0.4 ml of ethyl chloroformate (3.56 mmol, 1.1 eq) in 20 ml of dichloromethane is added to a solution of 1.0 g of 1-methoxy-4-(N,N-dimethylaminosulfonyl)-2-naphthalenecarboxylic acid (3.24 mmol, 1 eq) with 0.55 ml of triethylamine (3.88 mmol, 1.2 eq) in 70 ml of dichloromethane at 0° C. After 15 min, 0.74 g of 8-(phenylmethyl)-8-azabicyclo[3.2.1]octane-3-β-amine (3.4 mmol; 1.05 eq) in 20 ml of dichloromethane is added at 0 C. The mixture is left stirring at R.T. until all of the starting materials have been consumed. The mixture is washed three times with water, followed by saturated aqueous NaCl solution, after which it is dried and evaporated. 1.45 g (88%) of the pure product are obtained after flash chromatography on silica.

NMR (1H; $CDCl_3$): 1.65–1.87 (m; 4H); 1.96–2.15 (m; 4H), 2.93 (s; 6H; $N(CH_3)_2$), 3.32 (m; 2H; H1 and H5), 3.57 (s; 2H; N—$CH_2$—Ph); 4.00 (s; 3H; $OCH_3$), 4.48 (m; 1H; H3) 7.22–7.42 (m; 4H), 7.59–7.78 (m; 3H), 8.24 (dd, J=7.7, 2.3; 1H), 8.63 (s; 1H), 8.79 (dd, J=7.7, 2.3 Hz; 1H).

Preparation of the Salt:

644 mg of the base obtained (1.31 mmol, 1 eq) are dissolved in 4 ml of methyl ethyl ketone. 0.36 ml of a solution of HCl in isopropanol (3.65 N) is added. The precipitate formed is filtered off and dried.

Yield: 654 g (92%); m.p.: 196° C.; Formula: $C_{28}H_{34}ClN_3O_4S \cdot 0.1H_2O$; Molecular mass: base: 507.66; salt: 545.92

| | % C | % H | % N |
|---|---|---|---|
| Found | 61.78 | 6.38 | 7.53 |
| Calculated | 61.60 | 6.31 | 7.70 |

EXAMPLE 2

1,3-Dimethoxy-N-[8-(phenylmethyl)-8-azabicyclo[3.2.1] oct-3-β-yl]-2-naphthalenecarboxamide hydrochloride (Formula I: $R_1=CH_3$; $R_2=3$-$OCH_3$; $R_3=H$; Ar=Ph; n=1)

A solution of oxalyl chloride (0.412 ml; 4.74 mmol; 1.1 eq) in 20 ml of dichloromethane is added to a solution of 1,3-dimethoxy-2-naphthalenecarboxylic acid (1.0 g; 4.31 mmol; 1 eq) with a few drops of DMF in 90 ml of dichloromethane at 0° C. The mixture is then left stirring at R.T. for 1 h.

This solution obtained is added to a solution of 8-(phenylmethyl)-8-azabicyclo[3.2.1]octane-3-β-amine (0.979 g; 4.52 mmol; 1.05 eq) with 0.72 ml of triethylamine (5.17 mmol; 1.2 eq) in 20 ml of dichloromethane at 0° C. The mixture is then left stirring at R.T. until the reaction is complete. The reaction mixture is washed three times with water and then with saturated sodium chloride solution. The organic phase is dried and evaporated. The pure product is obtained after purification by flash chromatography on silica.

Yield: 0.375 g (20%) NMR (1H; CDCl$_3$): 1.67–1.89 (m; 4H); 1.97–2.12 (m; 4H), 3.31 (m; 2H; H1 and H5), 3.60 (s; 2H; N—CH$_2$—Ph); 3.88 (s; 3H; OCH$_3$), 3.98 (s; 3H; OCH3), 4.45 (m; 1H; H3), 7.20–7.49 (m; 8H), 7.68 (d, J=7.8 Hz; 1H), 7.99 (d; J=7.8 Hz; 1H).

Preparation of the Salt:

355 mg of the base obtained (0.82 mmol; 1 eq) are dissolved in 4 ml of methyl ethyl ketone. 0.23 ml of a solution of HCl in isopropanol (3.65 N) is added. The precipitate formed is filtered off and dried.

Yield: 341 mg (88%); m.p.: 124° C.; Formula: $C_{27}H_{30}N_2O_3 \cdot 0.9$ HCl.1H$_2$O; Molecular mass: base: 430.55; salt: 481.38

|  | % C | % H | % N |
|---|---|---|---|
| Found | 67.41 | 6.97 | 5.45 |
| Calculated | 67.32 | 6.89 | 5.82 |

EXAMPLE 3
1-Methoxy-N-[8-(phenylmethyl)-8-azabicyclo[3.2.1]oct-3-β-yl]-2-naphthalenecarboxamide The title compound is obtained in a similar manner to Stage 3 of Example 1, but starting with the corresponding reagents.

$R_1$=CH$_3$; Ar=Ph; $R_2$=$R_3$=H; n=1; $C_{26}H_{28}N_2O_2$; M.W.=400.53; m.p. ° C.=125

|  | % C | % H | % N |
|---|---|---|---|
| Found | 77.81 | 7.05 | 6.95 |
| Calculated | 77.97 | 7.05 | 6.99 |

EXAMPLE 4
4-Bromo-1-methoxy-N-[8-(phenylmethyl)-8-azabicyclo[3.2.1]oct-3-β-yl]-2-naphthalenecarboxamide oxalate The title compound is obtained in a similar manner to Stage 3 of Example 1, but starting with the corresponding reagents.

$R_1$=CH$_3$; Ar=Ph; $R_2$=4-Br; n=1; $R_3$=H; $C_{28}H_{29}BrN_2O_6$; M.W.=569.46; m.p. ° C.=193

|  | % C | % H | % N |
|---|---|---|---|
| Found | 58.99 | 5.19 | 4.84 |
| Calculated | 58.76 | 5.17 | 4.80 |

* +0.1 EtOAc

EXAMPLE 5
4-Chloro-1-methoxy-N-[8-(phenylmethyl)-8-azabicyclo[3.2.1]oct-3-β-yl)-2-naphthalenecarboxamide hydrochloride The title compound is obtained in a similar manner to Stage 3 of Example 1, but starting with the corresponding reagents.

$R_1$=CH$_3$; $R_2$=4-Cl; Ar=Ph; $R_3$=H; n=1; $C_{26}H_{29}Cl_2N_2O_2$; M.W.=472.44; m.p. ° C.=203

|  | % C | % H | % N |
|---|---|---|---|
| Found | 66.37 | 6.05 | 5.88 |
| Calculated | 66.07 | 6.14 | 5.93 |

EXAMPLE 6
1-Methoxy-4-(N,N-dimethylamino)-N-[8-(phenylmethyl)8-azabicyclo[3.2.1]oct-3-β-yl]-2-naphthalenecarboxamide oxalate The title compound is obtained in a similar manner to Stage 3 of Example 1, but starting with the corresponding reagents.

$R_1$=CH$_3$; $R_2$=4-N(CH$_3$)$_2$; Ar=Ph; $R_3$=H; n=1; $C_{31}H_{36}N_3O_8$; M.W.=578.65; m.p. ° C.=165; (0.4 H$_2$O); (585.85); (1.5 oxalate)

|  | % C | % H | % N |
|---|---|---|---|
| Found | 63.67 | 6.28 | 7.21 |
| Calculated | 63.53 | 6.33 | 7.17 |

EXAMPLE 7
4-Amino-1-methoxy-N-[8-(phenylmethyl)-8-azabicyclo[3.2.1]oct-3-β-yl]-2-naphthalenecarboxamide dioxalate The title compound is obtained in a similar manner to Stage 3 of Example 1, but starting with the corresponding reagents.

$R_1$=CH$_3$; $R_2$=4-NH$_2$; Ar=Ph; $R_3$=H; n=1; $C_{26}H_{29}N_3O_2$; M.W.=488.45; m.p.° C=189; 1.73 HCl; (510.88); (1.75 H$_2$O)

|  | % C | % H | % N |
|---|---|---|---|
| Found | 61.17 | 6.51 | 8.05 |
| Calculated | 61.13 | 6.75 | 8.22 |

EXAMPLE 8
1-Methoxy-4-nitro-N-[8-(phenylmethyl)-8-azabicyclo[3.2.1]oct-3-β-yl]-2-naphthalenecarboxamide hydrochloride The title compound is obtained in a similar manner to Stage 3 of Example 1, but starting with the corresponding reagents.

$R_1$=CH$_3$; $R_2$=4-NO$_2$; Ar=Ph; $R_3$=H; n=1; $C_{26}H_{28}ClN_3O_4$; M.W.=481.98; m.p. ° C.=192; (0.1 H$_2$O); (483.78)

|  | % C | % H | % N |
|---|---|---|---|
| Found | 64.31 | 5.84 | 8.47 |
| Calculated | 64.55 | 5.88 | 8.69 |

EXAMPLE 9
4-Cyano-1-methoxy-N-[8-(phenylmethyl)-8-azabicyclo[3.2.1]oct-3-β-yl]-2-naphthalenecarboxamide hydrochloride The title compound is obtained in a similar manner to Stage 3 of Example 1, but starting with the corresponding reagents.

$R_1$=CH$_3$; $R_2$=4-CN; Ar=Ph; $R_3$=H; n=1; $C_{27}H_{28}ClN_3O_2$; M.W.=462.00; m.p. ° C.=174; (0.2 H$_2$O); (465.59)

|  | % C | % H | % N |
|---|---|---|---|
| Found | 69.88 | 6.17 | 8.94 |
| Calculated | 69.65 | 6.15 | 9.03 |

EXAMPLE 10

1,5-Dimethoxy-N-[8-(phenylmethyl)-8-azabicyclo[3.2.1]oct-3-β-yl]-2-naphthalenecarboxamide hydrochloride The title compound is obtained in a similar manner to Stage 3 of Example 1, but starting with the corresponding reagents.

$R_1=CH_3$; $R_2=H$; $Ar=Ph$; $R_3=5-OCH_3$; n=1; $C_{27}H_{31}ClN_2O_3$; M.W.=466.72; m.p. °C.=216; (0.14 $H_2O$); (469.24)

|  | % C | % H | % N |
|---|---|---|---|
| Found | 69.12 | 6.75 | 5.90 |
| Calculated | 69.11 | 6.72 | 5.97 |

EXAMPLE 11

1,4-Dimethoxy-N-[8-(phenylmethyl)-8-azabicyclo[3.2.1]oct-3-β-yl]-2-naphthalenecarboxamide hydrochloride The title compound is obtained in a similar manner to Stage 3 of Example 1, but starting with the corresponding reagents.

$R_1=CH_3$; $R_2=4-OCH_3$; $Ar=Ph$; $R_3=H$; n=1; $C_{27}H_{31}ClN_2O_3$; M.W.=467.01; m.p. °C.=216

|  | % C | % H | % N |
|---|---|---|---|
| Found | 69.69 | 6.76 | 5.94 |
| Calculated | 69.44 | 6.69 | 6.00 |

EXAMPLE 12

1-Ethoxy-N-[8-(phenylmethyl)-8-azabicyclo[3.2.1]oct-3-β-yl]-2-naphthalenecarboxamide hydrochloride The title compound is obtained in a similar manner to Stage 3 of Example 1, but starting with the corresponding reagents.

$R_1=C_2H_5$; Ar=Ph; $R_2=R_3=H$; n=1; $C_{27}H_{31}ClN_2O_2$; M.W.=451.01; m.p. °C.=237; (0.1 $H_2O$); (452.81)

|  | % C | % H | % N |
|---|---|---|---|
| Found | 71.56 | 7.04 | 6.06 |
| Calculated | 71.62 | 6.95 | 6.18 |

EXAMPLE 13

4-Bromo-1-ethoxy-N-[8-(phenylmethyl)-8-azabicyclo[3.2.1]oct-3-β-yl]-2-naphthalenecarboxamide hydrochloride The title compound is obtained in a similar manner to Stage 3 of Example 1, but starting with the corresponding reagents.

$R_1=C_2H_5$; $R_2=4-Br$; Ar=Ph; $R_3=H$; n 1; $C_{27}H_{30}ClBrN_2O_2$; M.W.=529.91; m.p. °C.=215

|  | % C | % H | % N |
|---|---|---|---|
| Found | 61.35 | 5.70 | 5.32 |
| Calculated | 61.20 | 5.71 | 5.29 |

EXAMPLE 14

4-Acetamido-1-methoxy-N-[8-(phenylmethyl)-8-azabicyclo[3.2.1]oct-3-b-yl]-2-naphthalenecarboxamide hydrochloride The title compound is obtained in a similar manner to Stage 3 of Example 1, but starting with the corresponding reagents.

$R_1=CH_3$; Ar=Ph; $R_2=4-NHCOCH_3$; n=1; $R_3=H$; $C_{28}H_{32}ClN_3O_2$; M.W.=494.04; m.p. °C.=249; (0.2 $H_2O$); (497.63)

|  | % C | % H | % N |
|---|---|---|---|
| Found | 67.87 | 6.66 | 8.25 |
| Calculated | 67.58 | 6.56 | 8.44 |

EXAMPLE 15

4-Acetamido-1-methoxy-N-[8-(4-fluorophenylmethyl)-8-azabicyclo[3.2.1]oct-3-b-yl]-2-naphthalenecarboxamide hydrochloride The title compound is obtained in a similar manner to Stage 3 of Example 1, but starting with the corresponding reagents.

$R_1=CH_3$; Ar=4+F Ph; $R_2=4-NHCOCH_3$; n=1; $R_3=H$; $C_{28}H_{31}FClN_3O_3$; M.W.=494.04; m.p. °C.=249; (0.1 $H_2O$); (497.63)

|  | % C | % H | % N |
|---|---|---|---|
| Found | 67.87 | 6.66 | 8.25 |
| Calculated | 67.58 | 6.56 | 8.44 |

EXAMPLE 16

4-Acetamido-1-methoxy-N-[8-(4-chlorophenylmethyl)-8-azabicyclo[3.2.1]oct-3-b-yl]-2-naphthalenecarboxamide hydrochloride The title compound is obtained in a similar manner to Stage 3 of Example 1, but starting with the corresponding reagents.

$R_1=CH_3$; Ar=Ph; $R_2=4-NHCOCH_3$; n=1; $R_3=H$; $C_{28}H_{21}Cl_2N_3O_3$; M.W.=528.48; m.p. °C.=255; (0.4 $H_2O$); (535.68)

|  | % C | % H | % N |
|---|---|---|---|
| Found | 62.83 | 5.92 | 7.53 |
| Calculated | 62.78 | 5.98 | 7.84 |

EXAMPLE 17

4-Amino-1-methoxy-N-[8-(4-chlorophenylmethyl)-8-azabicyclo[3.2.1oct-3-b-yl]-2-naphthalenecarboxamide dihydrochloride The title compound is obtained in a similar manner to Stage 3 of Example 1, but starting with the corresponding reagents.

$R_1=CH_3$; $R_2$=4-$NH_2$; Ar=4-Cl Ph; $R_3$=H; n=1; $C_{26}H_{28}ClN_3O_2$1.9HCl; M.W.=519.26; m.p. ° C.=239; (0.5 $H_2O$); (528.26)

|  | % C | % H | % N |
|---|---|---|---|
| Found | 58.90 | 5.78 | 7.85 |
| Calculated | 59.11 | 5.89 | 7.95 |

EXAMPLE 18
4-Amino-1-methoxy-N-[8-(4-fluorophenylmethyl)-8-azabicyclo[3.2.1]oct-3-b-yl]-2-naphthalenecarboxamide dihydrochloride The title compound is obtained in a similar manner to Stage 3 of Example 1, but starting with the corresponding reagents.

$R_1=CH_3$; $R_2$=4-$NH_2$; Ar=4-F Ph; $R_3$=H; n=1; $C_{26}H_{28}FN_3O_2$1.95HCl; M.W.=504.63; m.p. ° C.=236; (0.6 $H_2O$); (515.44)

|  | % C | % H | % N |
|---|---|---|---|
| Found | 60.37 | 6.09 | 7.93 |
| Calculated | 60.59 | 6.09 | 8.15 |

EXAMPLE 19
4-Amino-1-ethoxy-N-[8-(phenylmethyl)-8-azabicyclo[3.2.1]oct-3-b-yl]-2-naphthalenecarboxamide dihydrochloride The title compound is obtained in a similar manner to Stage 3 of Example 1, but starting with the corresponding reagents.

$R_1=C_2H_5$; $R_2$=4-$NH_2$; Ar=Ph; $R_3$=H; n=1; $C_{27}H_{34}Cl_2N_3O_2$; M.W.=503.49; m.p. ° C.=230; (1 $H_2O$); (521.505)

|  | % C | % H | % N |
|---|---|---|---|
| Found | 62.27 | 6.84 | 8.02 |
| Calculated | 62.19 | 6.96 | 8.06 |

EXAMPLE 20
1-Ethoxy-4-fluoro-N-[8-(phenylmethyl)-8-azabicyclo[3.2.1]oct-3-b-yl]-2-naphthalenecarboxamide The title compound is obtained in a similar manner to Stage 3 of Example 1, but starting with the corresponding reagents.

$R_1=C_2H_5$; $R_2$=4-F; Ar=Ph; $R_3$=H; n=1; $C_{27}H_{30}FClN_2O_2$; M.W.=469.003; m.p. ° C.=223; (0.1 $H_2O$); (470.804)

|  | % C | % H | % N |
|---|---|---|---|
| Found | 68.86 | 6.43 | 5.86 |
| Calculated | 68.88 | 6.46 | 5.95 |

EXAMPLE 21
4-Fluoro-1-methoxy-N-[8-(phenylmethyl)-8-azabicyclo[3.2.1]oct-3-b-yl]-2-naphthalenecarboxamide hydrochloride The title compound is obtained in a similar manner to Stage 3 of Example 1, but starting with the corresponding reagents.

$R_1=CH_3$; $R_2$=4-F; Ar=Ph; $R_3$=H; n=1; $C_{26}H_{28}FClN_2O_2$; M.W.=454.98; m.p. ° C.=210; (0.1 $H_2O$); (456.77)

|  | % C | % H | % N |
|---|---|---|---|
| Found | 68.25 | 6.21 | 6.03 |
| Calculated | 68.37 | 6.22 | 6.13 |

EXAMPLE 22
4-Bromo-1-methoxy-N-[9-(phenylmethyl)-9-azabicyclo[3.3.1]non-3-b-yl]-2-naphthalenecarboxamide The title compound is obtained in a similar manner to Stage 3 of Example 1, but starting with the corresponding reagents.

$R_1=CH_3$; $R_2$=4-Br; Ar=Ph; $R_3$=H; n=2; $C_{26}H_{27}BrN_2O_2$; M.W.=479.43; m.p. ° C.=142

|  | % C | % H | % N |
|---|---|---|---|
| Found | 65.57 | 5.97 | 5.67 |
| Calculated | 65.72 | 5.92 | 5.68 |

EXAMPLE 23
4-Amino-1-methoxy-N-[9-(phenylmethyl)-9-azabicyclo[3.3.1]non-3-b-yl]-2-naphthalenecarboxamide dihydrochloride The title compound is obtained in a similar manner to Stage 3 of Example 1, but starting with the corresponding reagents.

$R_1=CH_3$; $R_2$=4-$NH_2$; Ar=Ph; $R_3$=H; n=2; $C_{27}H_{33}Cl_2N_3O_2$; M.W.=502.49; m.p. ° C.=260; (1.1 $H_2O$); (522.31)

|  | % C | % H | % N |
|---|---|---|---|
| Found | 62.25 | 6.92 | 7.93 |
| Calculated | 62.09 | 6.79 | 8.04 |

EXAMPLE 24
4-Bromo-1-methoxy-N-[8-(4-fluorophenylmethyl)-8-azabicyclo[3.2.1]oct-3-b-yl]-2-naphthalenecarboxamide oxalate The title compound is obtained in a similar manner to Stage 3 of Example 1, but starting with the corresponding reagents.

$R_1=CH_3$; $R_2$=4-Br; Ar=4-F Ph; $R_3$=H; n=1; $C_{28}H_{28}BrFN_2O_6$; M.W.=587.45; m.p. ° C.=149; (0.5 $H_2O$); (596.46)

|  | % C | % H | % N |
|---|---|---|---|
| Found | 56.61 | 4.76 | 4.77 |
| Calculated | 56.38 | 4.90 | 4.69 |

EXAMPLE 25
4-Bromo-1-methoxy-N-[8-(4-chlorophenylmethyl)-8-azabicyclo[3.2.1]oct-3-b-yl]-2-naphthalenecarboxamide oxalate The title compound is obtained in a similar manner to Stage 3 of Example 1, but starting with the corresponding reagents.

$R_1=CH_3$; $R_2$=4-Br; Ar=4-Cl Ph; $R_3$=H; n=1; $C_{28}H_{28}BrClN_2O_6$; M.W.=603.91; m.p. ° C.=138; (0.5 $H_2O$); (612.91)

|  | % C | % H | % N |
|---|---|---|---|
| Found | 54.77 | 4.60 | 4.61 |
| Calculated | 54.87 | 4.77 | 4.57 |

EXAMPLE 26

4-Methylthio-1-methoxy-N-[8-(phenylmethyl)-8-azabicyclo[3.2.1oct-3-b-yl]-2-naphthalenecarboxamide The title compound is obtained in a similar manner to Stage 3 of Example 1, but starting with the corresponding reagents.

$R_1=CH_3$; $R_2=4-SCH_3$; Ar=Ph; $R_3=H$; n=1; $C_{27}H_{30}N_2O_2S$; M.W.=446.61; m.p. ° C.=104

|  | % C | % H | % N |
|---|---|---|---|
| Found | 72.79 | 6.94 | 6.25 |
| Calculated | 72.91 | 6.77 | 6.27 |

EXAMPLE 27

4-Ethylthio-1-methoxy-N-[8-(phenylmethyl)-8-azabicyclo[3.2.1]oct-3-b-yl]-2-naphthalenecarboxamide The title compound is obtained in a similar manner to Stage 3 of Example 1, but starting with the corresponding reagents.

$R_1=CH_3$; $R_2=4-SC_2H_5$; Ar=Ph; $R_3=H$; n 1; $C_{28}H_{32}N_2O_2S$; M.W.=460.64; m.p. ° C.=82

|  | % C | % H | % N |
|---|---|---|---|
| Found | 73.05 | 7.13 | 5.97 |
| Calculated | 73.01 | 7.00 | 6.08 |

EXAMPLE 28

4-Ethylsulfonyl]-1-methoxy-N-[8-(phenylmethyl)-8-azabicyclo[3.2.1]oct-3-b-yl]-2-naphthalenecarboxamide The title compound is obtained in a similar manner to Stage 3 of Example 1, but starting with the corresponding reagents.

$R_1=CH_3$; $R_2=4-SO_2C_2H_5$; Ar=Ph; n 1; $R_3=H$; $C_{28}H_{32}N_2O_4S$; M.W.=492.64; m.p. ° C.=119; (1.36 $H_2O$); (483.20)

|  | % C | % H | % N |
|---|---|---|---|
| Found | 65.03 | 6.54 | 5.31 |
| Calculated | 65.03 | 6.76 | 5.41 |

EXAMPLE 29

4-Aminosulfonyl-1-methoxy-N-[8-(phenylmethyl)-8-azabicyclo[3.2.1oct-3-b-yl]-2-naphthalenecarboxamide The title compound is obtained in a similar manner to Stage 3 of Example 1, but starting with the corresponding reagents.

$R_1=CH_3$; $R_2=4-SO_2NH_2$; Ar=Ph; $R_3=H$; n=1; $C_{26}H_{29}N_3O_4S$; M.W. 479.60; m.p. ° C.=199; (0.2 $H_2O$); (483.20)

|  | % C | % H | % N |
|---|---|---|---|
| Found | 64.54 | 6.09 | 8.48 |
| Calculated | 64.63 | 6.13 | 8.69 |

EXAMPLE 30

4-Hydroxy-1-methoxy-N-[8-(phenylmethyl)-8-azabicyclo[3.2.1oct-3-b-yl]-2-naphthalenecarboxamide The title compound is obtained in a similar manner to Stage 3 of Example 1, but starting with the corresponding reagents.

$R_1=CH_3$; $R_2=4-OH$; Ar=Ph; $R_3=H$; n=1; $C_{26}H_{28}N_2O_3$; M.W.=416.52; m.p. ° C.=216; (0.1 $H_2O$); (418.33)

|  | % C | % H | % N |
|---|---|---|---|
| Found | 74.63 | 6.90 | 6.64 |
| Calculated | 74.65 | 6.79 | 6.69 |

EXAMPLE 31

4-Hydroxy-1-ethoxy-N-[8-(phenylmethyl)-8-azabicyclo[3.2.1]oct-3-b-yl]-2-naphthalenecarboxamide $R_1=C_2H_5$; $R_2=4-OH$; Ar=Ph; $R_3=H$; n=1; $C_{27}H_{30}N_2O_3$; M.W.=430.55

EXAMPLE 32

1-Methoxy-N-[9-(phenylmethyl)-9-azabicyclo[3.3.1]non-3b-yl]-2-naphthalenecarboxamide hydrochloride The title compound is obtained in a similar manner to Stage 3 of Example 1, but starting with the corresponding reagents.

$R_1=CH_3$; $R_2=H$; Ar=Ph; $R_3=H$; n=2; $C_{27}H_{31}ClN_2O_2$; M.W.=451.01; m.p. ° C.=232; (0.25 $H_2O$); (455.51)

|  | % C | % H | % N |
|---|---|---|---|
| Found | 70.93 | 7.22 | 6.10 |
| Calculated | 71.19 | 6.97 | 6.15 |

EXAMPLE 33

1-Ethoxy-4-nitro-N-[8-(phenylmethyl)-8-azabicyclo[3.2.1]oct-3-b-yl]-2-naphthalenecarboxamide hydrochloride The title compound is obtained in a similar manner to Stage 3 of Example 1, but starting with the corresponding reagents.

$R_1=C_2H_5$; $R_2=4-NO_2$; Ar=Ph; $R_3=H$; n=1; $C_{27}H_{30}ClN_3O_4$; M.W.=496.01; m.p. ° C.=187

|  | % C | % H | % N |
|---|---|---|---|
| Found | 65.26 | 6.14 | 8.43 |
| Calculated | 65.38 | 6.10 | 8.47 |

We claim:
1. A compound selected from those of formula I

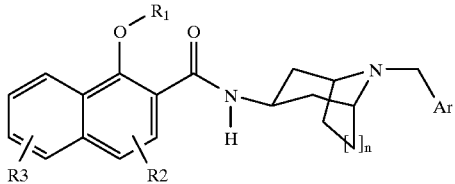

in which Ar represents an aromatic residue such as, for example, a phenyl or heteroaryl ring, the phenyl ring being unsubstituted or substituted with one or more substituents chosen from $C_{1-4}$ alkyl, Cl, F, Br, or $C_{1-4}$ O-alkyl, n is one or two, thus forming an 8-azabicyclo-[3.2.1]octane or a 9-azabicyclo-[3.3.1]nonane, $R_1$ is a linear or branched $C_{1-6}$ alkyl group, $R_2$ and $R_3$, which may be identical or different, are H, Cl, Br, F, $C_{1-4}$ alkyl, OH, CN, $NO_2$, $C_{1-4}$ S-alkyl, $NH_2$, $C_{1-4}$ NH-alkyl, $C_{1-4}$ N-dialkyl, NH-acyl, $SO_2NH_2$, $C_{1-4}$ $SO_2$N-dialkyl or $C_{1-4}$ $SO_2$-alkyl, and addition salts thereof with a pharmaceutically-acceptable inorganic or organic acid.

2. A compound of claim 1, wherein $R_1$ is an methoxy or an ethoxy, $R_2$ is Cl, Br, F, $NH_2$, $NMe_2$, OH, Ar, or a phenyl substituted with a halogen Cl or F.

3. A compound of claim 1, chosen from the group consisting of the following compounds and the addition salts thereof with a pharmaceutically-acceptable inorganic or organic acid:

1,3-dimethoxy-N-[8-(phenylmethyl)-8-azabicyclo[3.2.1]oct-3-b-yl]-2-naphthalenecarboxamide 1-methoxy-N-[8-(phenylmethyl)-8-azabicyclo[3.2.1]oct-3-b-yl]-2-naphthalenecarboxamide 4-bromo-1-methoxy-N-[8-(phenylmethyl)-8-azabicyclo[3.2.1]oct-3-b-yl]-2-naphthalenecarboxamide 4-chloro-1-methoxy-N-[8-(phenylmethyl)-8-azabicyclo[3.2.1]oct-3-b-yl]-2-naphthalenecarboxamide 1-methoxy-4-(N,N-dimethylamino)-N-[8-(phenylmethyl)-8-azabicyclo[3.2.1]oct-3-b-yl]-2-naphthalenecarboxamide 4-amino-1-methoxy-N-[8-(phenylmethyl)-8-azabicyclo[3.2.1]oct-3-b-yl]-2-naphthalenecarboxamide 1-methoxy-4-nitro-N-[8-(phenylmethyl)-8-azabicyclo[3.2.1]oct-3-b-yl]-2-naphthalenecarboxamide 4-cyano-1-methoxy-N-[8-(phenylmethyl)-8-azabicyclo[3.2.1]oct-3-b-yl]-2-naphthalenecarboxamide 1,5-dimethoxy-N-[8-(phenylmethyl)-8-azabicyclo[3.2.1]oct-3-b-yl]-2-naphthalenecarboxamide 1,4-dimethoxy-N-[8-(phenylmethyl)-8-azabicyclo[3.2.1]oct-3-b-yl]-2-naphthalenecarboxamide 1-ethoxy-N-[8-(phenylmethyl)-8-azabicyclo[3.2.1]oct-3-b-yl]-2-naphthalenecarboxamide 4-bromo-1-ethoxy-N-[8-(phenylmethyl)-8-azabicyclo[3.2.1]oct-3-b-yl]-2-naphthalenecarboxamide 4-acetamido-1-methoxy-N-[8-(phenylmethyl)-8-azabicyclo[3.2.1]oct-3-b-yl]-2-naphthalenecarboxamide 4-acetamido-1-methoxy-N-[8-(4-fluorophenylmethyl)-8-azabicyclo[3.2.1]oct-3-b-yl]-2-naphthalenecarboxamide 4-acetamido-1-methoxy-N-[8-(4-chlorophenylmethyl)-8-azabicyclo[3.2.1]oct-3-b-yl]-2-naphthalenecarboxamide 4-amino-1-methoxy-N-[8-(4-chlorophenylmethyl)-8-azabicyclo[3.2.1]oct-3-b-yl]-2-naphthalenecarboxamide 4-amino-1-methoxy-N-[8-(4-fluorophenylmethyl)-8-azabicyclo[3.2.1]oct-3-b-yl]-2-naphthalenecarboxamide 4-amino-1-ethoxy-N-[8-(4-fluorophenylmethyl)-8-azabicyclo[3.2.1]oct-3-b-yl]-2-naphthalenecarboxamide 4-fluoro-1-ethoxy-N-[8-(phenylmethyl)-8-azabicyclo[3.2.1]oct-3-b-yl]-2-naphthalenecarboxamide 4-fluoro-1-methoxy-N-[8-(phenylmethyl)-8-azabicyclo[3.2.1]oct-3-b-yl]-2-naphthalenecarboxamide 4-bromo-1-methoxy-N-[9-(phenylmethyl)-9-azabicyclo[3.3.1]non-3-b-yl]-2-naphthalenecarboxamide 4-amino-1-methoxy-N-[9-(phenylmethyl)-9-azabicyclo[3.3.1]non-3-b-yl]-2-naphthalenecarboxamide 4-bromo-1-methoxy-N-[8-(4-fluorophenylmethyl)-8-azabicyclo[3.2.1]oct-3-b-yl]-2-naphthalenecarboxamide 4-bromo-1-methoxy-N-[8-(4-chlorophenylmethyl)-8-azabicyclo[3.2.1]oct-3-b-yl]-2-naphthalenecarboxamide 4-methylthio-1-methoxy-N-[8-(phenylmethyl)-8-azabicyclo[3.2.1]oct-3-b-yl]-2-naphthalenecarboxamide 4-ethylthio-1-methoxy-N-[8-(phenylmethyl)-8-azabicyclo[3.2.1]oct-3-b-yl]-2-naphthalenecarboxamide 4-ethylsulfonyl-1-methoxy-N-[8-(phenylmethyl)-8-azabicyclo[3.2.1]oct-3-b-yl]-2-naphthalenecarboxamide 4-aminosulfonyl-1-methoxy-N-[8-(phenylmethyl)-8-azabicyclo[3.2.1]oct-3-b-yl]-2-naphthalenecarboxamide 4-hydroxy-1-methoxy-N-[8-(phenylmethyl)-8-azabicyclo[3.2.1]oct-3-b-yl]-2-naphthalenecarboxamide 4-hydroxy-1-ethoxy-N-[8-(phenylmethyl)-8-azabicyclo[3.2.1]oct-3-b-yl]-2-naphthalenecarboxamide 1-methoxy-N-[9-(phenylmethyl)-9-azabicyclo[3.3.1]non-3b-yl]-2-naphthalenecarboxamide 1-ethoxy-4-nitro-N-[8-(phenylmethyl)-8-azabicyclo[3.2.1]oct-3b-yl]-2-naphthalenecarboxamide.

4. Process for preparing a compound of formula I according to claim 1, wherein starting a naphthenic acid having the substituents $R_1$, $R_2$ and $R_3$ according to claim 1 is reacted with 3β-amino-8-benzyl]-8-azabicyclo[3.2.1]octane or 3β-amino-9-benzyl]-9-azabicyclo[3.3.1]nonane under coupling conditions using alkyl chloroformate in the presence of triethylamine in methylene chloride at low temperature, or using the acid chloride of the corresponding starting naphthenic acid.

5. Pharmaceutical composition comprising at least one compound according to claims 1 and a pharmaceutically-acceptablr excipient.

6. Method for the treatment of a condition selected from schizophrenia, its positive and negative symptoms, compulsive obsessive disorders, anxiety, depression, drug addiction, tardive dyskinesia, and gastrointestinal disorders, comprising the step of administering to a living body suffering from such condition an amount of a compound of claim 1 which is effective for alleviation of such condition.

7. Pharmaceutical composition comprising at least one compound according to claim 2 and a pharmaceutically-acceptable excipient.

8. Pharmaceutical composition comprising at least one compound according to claim 3 and a pharmaceutically-acceptable excipient.

9. Method for the treatment of a condition selected from schizophrenia, its positive and negative symptoms, compulsive obsessive disorders, anxiety, depression, drug addiction, tardive dyskinesia, and gastrointestinal disorders, comprising the step of administering to a living body suffering from such condition an amount of a compound of claim 2 which is effective for alleviation of such condition.

10. Method for the treatment of a condition selected from schizophrenia, its positive and negative symptoms, compulsive obsessive disorders, anxiety, depression, drug addiction, tardive dyskinesia, and gastrointestinal disorders, comprising the step of administering to a living body suffering from such condition an amount of a compound of claim 3 which is effective for alleviation of such condition.

* * * * *

UNITED STATES PATENT AND TRADEMARK OFFICE
CERTIFICATE OF CORRECTION

PATENT NO. : 5,958,945
DATED : Sept. 28, 1999
INVENTOR(S) : T. Imbert, B. Monse, W. Koek Page 1 of 2

It is certified that error appears in the above-indentified patent and that said Letters Patent is hereby corrected as shown below:

Column 3, line 51: "$C^{1-6}$" should read -- $C_{1-6}$ --.

Column 8, line 41: Insert -- ; -- after "H3)" at the

Column 12, line 63: "azabicyclo[3.2.1" should read -- azabicyclo [3.2.1] --.

Column 15, line 11: "azabicyclo[3.2.1" should read -- azabicyclo[3.2.1] --.

Column 15, line 61: "azabicyclo[3,2,1" should read -- azabicyclo[3,2,1] --, Page 31, line 24

Column 16, line 12: At the beginning of the line, "[3.2.1" should read -- [3.2.1] --.

Column 17, line 28: Delete the word "an".

Column 17, line 28: Delete the "a" before "phenyl".

Column 17, line 29: Delete the words "a halogen"

UNITED STATES PATENT AND TRADEMARK OFFICE
CERTIFICATE OF CORRECTION

PATENT NO. : 5,958,945
DATED : Sept. 28, 1999
INVENTOR(S) : T. Imbert, B. Monse, W. Koek It is certified that error appears in the above-indentified patent and that said Letters Patent is hereby corrected as shown below:

Column 18, line 38:  Delete the "]" after aminosulfonyl]

Column 18, line 46:  Insert the word -- and -- at the end of the line.

Column 18, line 59:  "claims" should read -- claim --. Page 3 of Preliminary Amendment dtd 3/12/98, Claim 6, line 3.

Column 18, line 60:  "acceptablr" should read as -- acceptable --.

Signed and Sealed this

Fifth Day of September, 2000

Attest:

Attesting Officer

Q. TODD DICKINSON

Director of Patents and Trademarks